United States Patent [19]

Stasz et al.

[11] 4,122,713

[45] Oct. 31, 1978

[54] LIQUID VELOCITY MEASURING SYSTEM

[75] Inventors: Peter Stasz, Minneapolis; Floyd R. Patten, Stacy, both of Minn.

[73] Assignee: Medtronic, Inc., Minneapolis, Minn.

[21] Appl. No.: 798,670

[22] Filed: May 19, 1977

[51] Int. Cl.$^2$ .............................................. G01F 1/66
[52] U.S. Cl. ..................................... 73/194 A; 73/19; 128/2 V; 128/2.05 Z
[58] Field of Search .................. 73/194 A, 67.6, 67.7, 73/19, 61 R; 128/2 V, 2.05 F, 2.05 Z, 214 E, DIG. 13; 340/237 R

[56] References Cited

U.S. PATENT DOCUMENTS

| | | | |
|---|---|---|---|
| 3,741,014 | 6/1973 | Tamura | 73/67.7 X |
| 3,812,482 | 5/1974 | Clark | 128/214 E |
| 3,921,622 | 11/1975 | Cole | 73/61 R X |
| 3,974,681 | 8/1976 | Namery | 73/19 X |

OTHER PUBLICATIONS

Jacobson et al., "Ultrasonic Detection of Bloodstream Emoli"-IEEE International Conference on Engineering in the Ocean Environment, Sep. 1973, pp. 141-147.

*Primary Examiner*—Charles A. Ruehl
*Attorney, Agent, or Firm*—R. Lewis Gable; Joseph F. Breimayer

[57] ABSTRACT

A liquid velocity measuring system is described utilizing ultrasonic waves to measure the velocity of a liquid and in particular, the velocity of blood as directed through a conduit external of the patient's body. The liquid velocity measuring system comprises an ultrasonic soundwave transmitting transducer energized by a continuous wave generator, preferably at a frequency of 3.13 MHz. The transmitting transducer is disposed with respect to the conduit such that the transmitted ultrasonic waves are backscattered or reflected from ultrasonic reflection centers in the blood. This signal is received and detected by a second ultrasonic transducer. The reflected ultrasonic wave is frequency-shifted dependent upon the velocity of the liquid directed through the conduit and is detected by the second transducer to be amplified and demodulated subsequently, before being applied to a microbubble detection circuit in accordance with the teachings of this invention. In particular, the microbubble detection circuit rectifies and filters the backscattered signal before applying it to a comparator circuit. In the presence of microbubbles within the liquid, the reflected ultrasonic wave will increase in amplitude at least 15-fold over that liquid, and in particular, blood without microbubbles. The comparator is set to provide an output signal if the strength of the detected signal increases 15-fold, to provide an output signal for setting a flip-flop whose output in turn energizes an alarm indicative of the presence of microbubbles.

12 Claims, 3 Drawing Figures

U.S. Patent  Oct. 31, 1978  Sheet 1 of 2  4,122,713
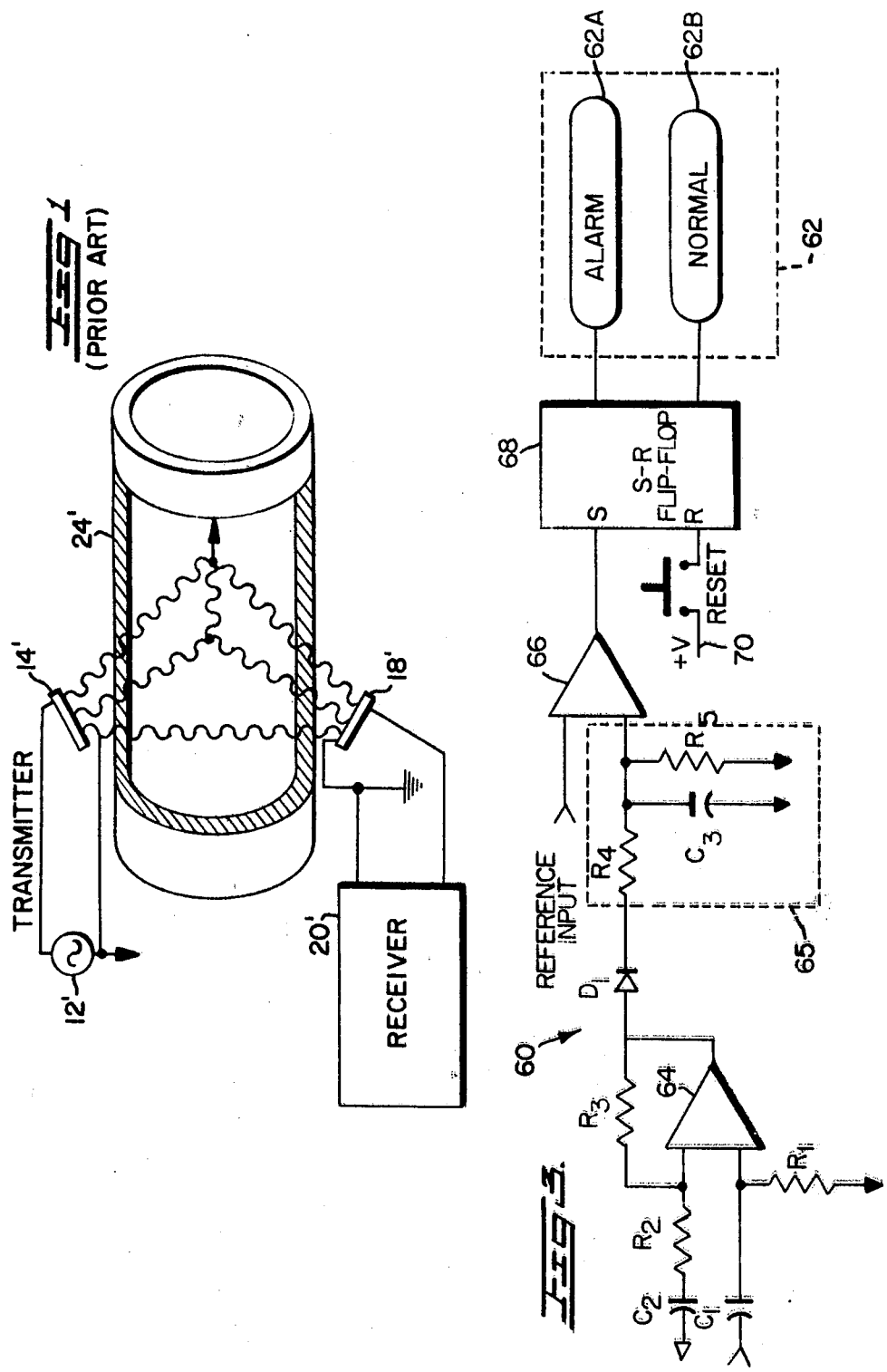

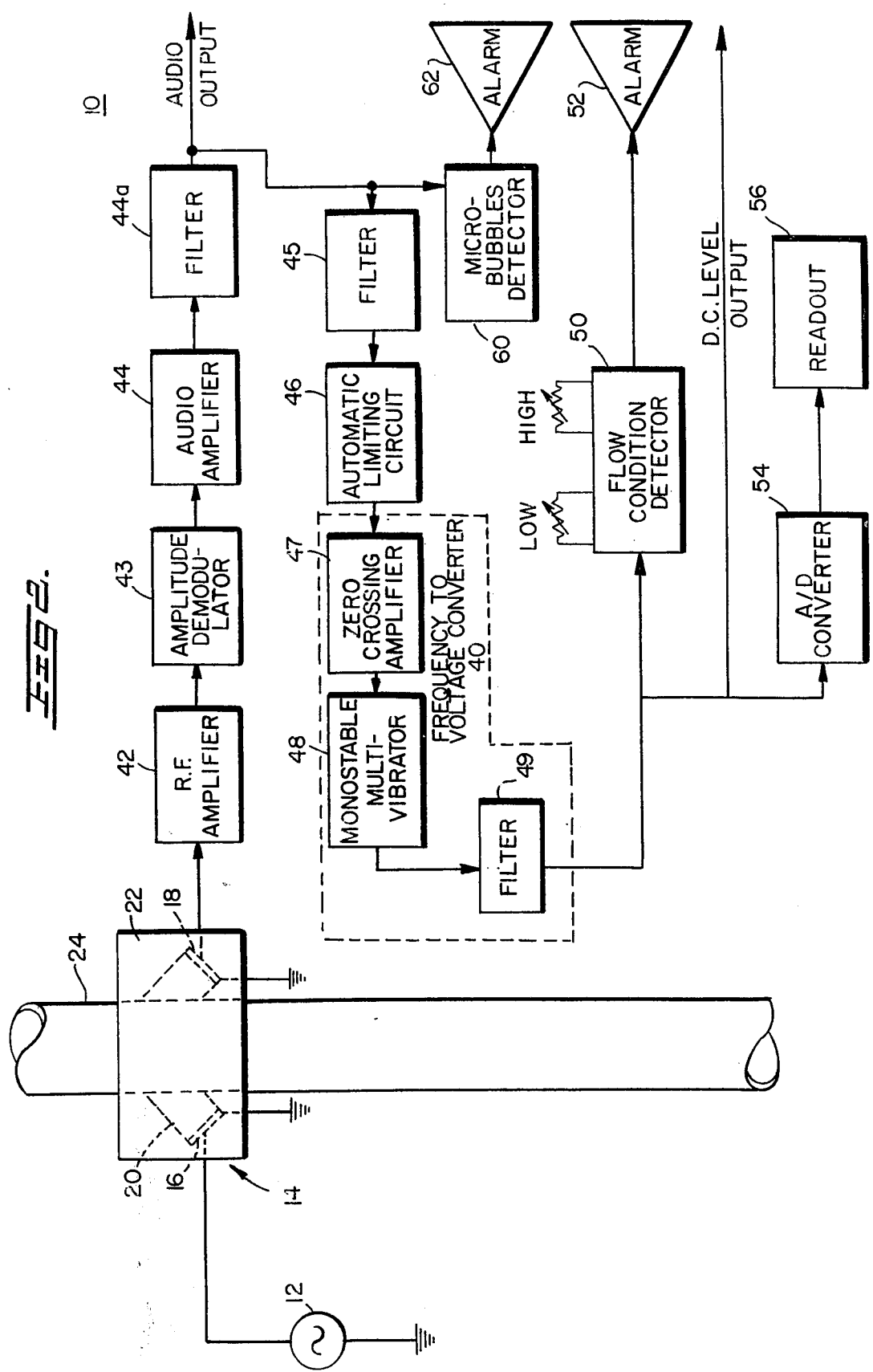

LIQUID VELOCITY MEASURING SYSTEM

BACKGROUND OF THE INVENTION

1. Field of the Invention

This invention relates to systems for measuring liquid velocity and in particular for measuring blood velocity on backscatter Doppler principles, and to detect the presence of bubbles within the blood.

2. Description of the Prior Art

It is known to use ultrasonic devices for measurement of the speed of a liquid flow in general. These devices, most of which use two transducers, or sometimes a single transducer, use the Doppler effect. Devices are also known which apply the same principle to blood flow rate measurement. The known devices are speed meters; see particularly the articles by Franklin and collaborators in "The American Journal of Medical Electronics", 1st term 1966, pages 24–28 and "IRE Transactions of Bio-medical Electronics", January 1962, pages 44–49. As shown in FIG. 1, such ultrasonic devices typically included an ultrasonic transducer illustratively in the form of a crystal $14'$ that is energized by a generator $12'$ to emit ultrasonic waves into a conduit $24'$, whereby it is reflected by the liquid directed therethrough to be sensed by a detector, typically in the form of a crystal $18'$, the output of which is connected to a receiver $20'$. The receiver $20'$ as will be explained below, detects the received Doppler signal which contains the velocity information. In the particular, illustrative context of this invention, such principles are used to measure the velocity of blood as would be directed through a conduit external of the patient's body. In one illustrative embodiment of this invention, it is contemplated that a heart assist machine would be used to aid the patient's heart and that the blood flow through this machine could be measured in accordance with the teachings of this invention.

The practical application of the Doppler backscatter principle consists of transmitting an ultrasonic beam into the medium whose velocity one wishes to measure and to compare the original frequency with the received shifted frequency. To retrieve the velocity information, a comparison of the scattered signal frequency with the original frequency is made by the receiver $20'$. The difference in frequency is related to the flow velocity of the medium. Since the medium is flowing generally in a conduit of known dimension, the velocity information can be translated into total flow rate.

There are two basic aspects to this phenomena; the particle size can be larger than the wavelength of the transmitting ultrasound or it can be smaller, therefore acting as a point scatterer. It is noted that the red cells of blood have a typical diameter of 8 $\mu$m thickness of 2 $\mu$m, with the wavelength of the 3.13 MHz ultrasonic beam being approximately 480 $\mu$m in blood. In the case of red cells, the cell is smaller than the wavelength of the beam and the cell is set into motion and becomes a secondary emitter acting as a point source.

The envelope of the received signal represents the heterodyne coupling of the transmitted carrier with the backscattered signal whose normal frequency has been shifted by the Doppler phenomena. This signal then is amplified, demodulated, audio amplified, processed and displayed as flow rate by the receiver $20'$, as shown in FIG. 1. The shift in frequency is due to the relative motion of the object with respect to the transmitter and receiver. The frequency shift due to motion of the particle with respect to the transmitter is:

$$f_1 = f_c \frac{V_0 - V\cos\theta}{V_0} \tag{1}$$

where $f_1$ = Frequency of the forced particle oscillation
$V_O$ = Ultrasound velocity in medium
$V$ = Particle velocity
$\theta$ = Angle between the ultrasound and the velocity vector
$f_c$ = Ultrasonic carrier frequency The frequency shift due to motion of the particle with respect to the receiver is:

$$f_2 = f_1 \frac{V_0}{V_0 + V\cos\theta} \tag{2}$$

where $f_1$ = frequency of the forced particle oscillation
$f_2$ = New frequency as measured at the receiver
$V_O$, $V$, $O$ as indicated above Combining (1) and (2), the total Doppler shift may be exposed as:

$$f = (f_c - f_1) + (f_1 - f_2) = f_c - f_2 \tag{3}$$

$$f = f_c\left(1 - \frac{V_0 - V\cos\theta}{V_0 + V\cos\theta}\right) \tag{4}$$

The formula can be expanded in a series and only the most important term taken when $V_O(1500 \text{ m/sec}) >> V (<1.5 \text{ m/sec at } 10 \text{ L/minute})$, to provide the expression:

$$f = 2\, Vf_c \cos\theta/V_O \tag{5}$$

This is the general formula used in the backscatter Doppler flowmeter design. This signal is difficult to detect since the signal amplitude at this shifted frequency is small and becomes swamped by the direct coupled ultrasonic carrier frequency. Fortunately, the direct radiated ultrasonic wave received is mixed with the backscatter signal in the crystal $18'$ producing an amplitude modulated signal that retains all the basic information as indicated by formula (5). The receiving crystal $18'$ converts the ultrasonic energy back into an electrical signal. The amplitude modulated signal, at microvolt levels, is RF amplified, detected, audio amplified, processed and displayed as flow information.

When an ultrasonic device is used to measure blood flow external of the human body and in particular in the situation where such a device is used to measure the velocity of blood flowing to a heart assist device, it is contemplated that a supply of air bubbles may be accidently introduced into a blood flow and subsequently into the patient's body, with the possible result that such bubbles would be introduced via the arterial portion of the patient's cardiovascular system into his brain. Such bubbles tend to block the flow of blood through the smaller arteries, thus leading to possible brain tissue damage and ultimately stroke and death.

Thus, it is a principal object of this invention to provide means for sensing the presence of air or other gaseous bubbles within the blood flow to provide a suitable alarm manifestation indicative thereof, whereby attending personnel may check the heart assist equipment for any malfunction and also take appropriate remedial action with respect to the patient.

The air bubble detection system of this invention differs from that blood flow pressure measurement system as described in U.S. Pat. No. 3,640,271, wherein bubbles of a controlled diameter are introduced into a patient's bloodstream to permit detection by ultrasonic devices at first and second points to provide an indication of the blood velocity, dependent upon the time it took for the bubbles to move away from the first to the second point. At the first point, the bubble is subjected to energy at or near its resonant frequency, and at the second point, the bubbles are detected by subjecting them to ultrasonic waves to excite them to the resonant frequency and detecting at the second point backscattered energy indicative of the passage of the bubbles. The noted U.S. Pat. No. 3,640,271 does not contemplate a first or normal mode of operation, wherein Doppler principles are used for measuring blood flow velocity, and a second mode of operation for detecting the inadvertent injection of bubbles into the bloodstream and providing an alarm indicative thereof. In this regard, the inadvertently introduced bubbles may be of a size detrimental to the patient and the system of this invention operates to distinguish normal and abnormal conditions to provide an alarm indicative thereof.

SUMMARY OF THE INVENTION

It is therefore an object of this invention to provide a system for measuring liquid velocity and additionally having the capability of detecting the presence of gases, and in particular air bubbles, therein.

It is a more particular object of this invention to provide a system for measuring blood velocity, having the capability of providing an alarm manifestation indicative of the presence of air bubbles in the blood.

In accordance with these and other objections of the invention, there is provided a system utilizing Doppler techniques for measuring the velocity of a liquid directed through a conduit, including a transducer for receiving energy reflected from the liquid and further including a detector responsive to an increase in the output of the aforementioned transducer to energize an alarm indicative of the presence of gaseous bubbles carried by the liquid.

In a particular embodiment of this invention, this system is adapted to measure the velocity of blood directed externally of the patient's body, having a detector comprising a comparator for sensing a relatively high increase in the transducer output indicative of the presence of bubbles in the blood. In a particular embodiment of this invention, the output of the comparator is applied to a memory such as a flip-flop circuit, whereby the detector circuit may continue to energize an alarm until it is is reset by an operator. In an illustrative embodiment of this invention, the comparator is adapted to sense a 15-fold increase in the output of the transducer to energize the aforementioned alarm.

BRIEF DESCRIPTION OF THE DRAWINGS

These and other objects and advantages of the present invention will become more apparent by referring to the following detailed description and accompanying drawings, in which:

FIG. 1 is a description of a prior art transducer illustrating the general principles of a Doppler-type liquid flow measuring system;

FIG. 2 is a schematic diagram of a liquid velocity measuring system including a detector for sensing the detection of gaseous bubbles within the liquid to energize a suitable alarm indicative thereof, in accordance with the teachings of this invention; and FIG. 3 is a schematic diagram showing in more detail the circuitry of the microbubble detector as generally shown in FIG. 2.

DETAILED DESCRIPTION OF THE PREFERRED EMBODIMENT

With regard to the drawings and in particular to FIG. 2, there is shown a liquid velocity measuring system 10, including a continuous wave generator 12 for energizing a transmitting transducer 16 to emit energy in the form of ultrasonic waves toward and into the liquid, whose velocity is to be measured, as directed through a conduit 24 past transducer 16. Energy is reflected or scattered from the moving liquid, to be detected by a receiver in the form of a crystal 18, which converts the transmitted ultrasonic waves into an electrical signal of a frequency in the order of 2-3 MHz that is applied to an RF amplifier 42, which is adapted to amplify signals of such frequencies and applies its amplified output to an amplitude demodulator circuit 43. The transmitter transducer and receiver transducers 16 and 18 are mounted about the conduit 24 by an assembly 14. The transducer assembly 14 includes the transmitting transducer 16 and the receiving transducer 18, each made of a lead titanium zirconate (LTZ) one-inch square that is cut to approximate dimensions of $0.3 \times 0.5$ inch and mounted, respectively, within the top housing 20 and the bottom housing 22 of the assembly 14. In an illustrative embodiment of this invention, the transmitting transducer 16 was selected to be LTZ-1 material with the receiving crystal 18 an LTZ-5, whereby the entire system sensitivity was improved by a factor of approximately 2 over an embodiment where the transmitting transducer 16 was also made of an LTZ-5 material. The demodulator circuit output is applied to an audio amplifier 44, which may also include a high-frequency filter 44a to filter out undesired high frequencies. In particular, it has been found that the output of the demodulator 43 contained undesirable higher frequency, noise components mixed with the audio component carrying the desired velocity information. This undesirable higher frequency noise component varies within the frequency range of interest, tending to hide the information bearing component. As a result, it may be necessary to incorporate the filter 44a to eliminate this higher frequency noise component.

The envelope of the signal received by the crystal 18 represents the heterodyne coupling of the carrier of the transmitted energy or ultrasonic waves with the backscattered signal, whose normal frequency has been shifted by the Doppler phenomenon, in accordance with the velocity of the liquid directed through conduit 24. In essence, the demodulator 43 provides an output in accordance with the envelope of the received signal, which in turn is applied to the audio amplifier 44 to amplify the detected audio signal.

The output of the audio amplifier is applied to a microbubble detector 60 in accordance with teachings of this invention, which senses an increase in the output indicative of the presence of microbubbles to energize an alarm 62 to provide a suitable manifestation thereof. In addition, the audio amplifier output also is applied to a filter 45 for passing a rather narrow band of frequency, e.g. 45-4800 Hz. At the low end, the filter 45 eliminates those frequency components resulting from the conduit motion due to the pulsing blood flow therethrough. The filter 45 also removes high-frequency components due to the electronic noise of the circuitry preceding the filter 45, as described above. The filtered output of the filter 45 in turn is applied to an automatic limiting circuit 46, which generally smoothes out or limits the amplitude of the signal which in turn is applied to a frequency-to-voltage converter 40. As the velocity of the liquid flowing through the conduit 24 increases, turbulences within the fluid develop, causing possible reverse flow of the fluid. The receiver 18 is unable to distinguish the forward and reverse flows of the fluid, and the receiver output, particularly at the lower frequencies, increases in amplitude, tending to suppress the higher-frequency components of less amplitude, which contain the information indicative of the velocity of the fluid flow. The automatic amplitude limiting circuit 46 tends to suppress the amplitude of these lower-frequency components so that its output signal provides a more accurate indication of the velocity flow through the conduit 24. In turn, the output of the automatic limiting circuit is applied to a frequency-to-voltage circuit 40, which provides an output to a flow condition detector 50 which is actuated upon detection of a signal below a first, low limit or above a second, high limit to energize an alarm 52.

As shown in FIG. 2, the frequency-to-voltage circuit 40 comprises a zero crossing amplifier with hysteresis 47, which provides a sharp triggering signal to a monostable multivibrator 48, thus preventing the false generation of such triggering signals as might otherwise occur due to the presence of the noise or jitter in the output of the receiving crystal 18. Basically, in order to provide an accurate frequency-to-voltage converter 40, the pulse height and width of the signals must be standardized, which function is carried out by the monostable multi-vibrator 48, whose output then is applied to a filter 49, which integrates the monostable multivibrator output 48 to provide a DC signal to the flow condition detector 50 and to an A/D converter 54. The analog-to-digital converter 54 in turn actuates a digital readout or display 56 to provide a manifestation of the liquid velocity. The high/low flow condition detector 50 provides a safety means whereby circuit malfunction, improper probe integrity and very low flow conditions can result in an alarm signal. Under such conditions, the alarm 52 is actuated to provide a visual and/or sound manifestation of such a deficient condition. In particular, if the signal as derived from the transducer 18 is too low, this may be an indication that the probe is not connected, there is no flow or the coupling adhesive that is disposed to effect an acoustical coupling between a transducer and the conduit 24 has dried out. The flow condition detector 50 responds to the output of the frequency-to-voltage converter 40 above predetermined level corresponding to a condition wherein the artificial blood pump directing blood into the patient is out of control and is running at a rate higher than that desired for the patient, i.e. the rate of blood flow may be so great as to cause possible rupture of the patient's arteries. In an illustrative embodiment of this invention, the flow condition detector 50 responds to a low condition corresponding to a flow of less than 2 liters/min. to provide a low alarm signal, and to a high condition corresponding to a flow of greater than 6 liters/min. to provide a high alarm signal; the illustrative limits are set for a system including a conduit 24 of one-half inch diameter; as attached to the left ventricular aorta of a patient. It is noted that these limits are dependant upon the particular application and in particular, to which artery the conduit 24 is coupled, noting that for smaller arteries, the velocity of the blood increases.

In an illustrative embodiment of this invention, the generator 12 was selected to be an oscillator as manufactured by Hewlett-Packard under their number HP606B and its output frequency was determined empirically; the optimum frequency of the generator 12 was selected to be 3.13 MHz as a compromise between attenuation and resolution. It was found that as higher frequencies were used, attenuation was increased unduly, though resolution was improved. Thus, in the measurement of blood flow, red cells have a typical diameter of 8 micrometer and a thickness of 2 micrometer, so that the wavelength of the selected 3.13 MHz ultrasonic beam would be approximately 480 micrometer in blood. As a result, the red cells have a smaller diameter than the wavelength of the ultrasonic beam and the red cell is set into motion, thus becoming a secondary emitter acting as a point source whereby energy is radiated toward the receiving crystal 18. Thus, the envelope of the electrical output signal provided by the crystal 18 represents the heterodyne coupling of the transmitted carrier signal as derived from the transmitting crystal 16 with the backscattered signal whose normal frequency has been shifted by the Doppler phenomenon. The receiving crystal 18 converts the ultrasonic energy back into an electrical signal, which is amplitude modulated at microvolts level.

The detection amplification of the signal derived from the receiving crystal 18 presented various problems, one due primarily to the large range of amplitude of the signals derived from the crystal 18. In this regard, the amplifier 42 and the demodulator 43 are designed to handle a large dynamic range and, in an illustrative embodiment of this invention, are formed of discrete parts, as opposed to being formed of a single integrated circuit, to provide low noise amplification, capable of handling a gain of approximately $10^3$, without saturation. By using discrete components with a low noise preamplifier, a system gain may be obtained from the amplifier 42 and the amplifier 44 of about $10^5$ without at the same time making the noise produce false readout.

Further, the carrier signal as derived from the receiving crystal 18 changes in amplitude when the distance between the transmitting and receiving crystals 16 and 18 varies in multiples of acoustical halfwavelengths, as their positions would be adjusted with respect to the conduit 24. The magnitude of the signal change between maximum and minimum was observed to be as large as 10-to-1. By contrast, the amplitude modulation as imposed upon the carrier signal due to the liquid flow, is less than 0.5% with the amplitude of the Doppler signal being in the order of 10 microvolts, while the amplitude of the carrier signal is in the millivolt range. Thus, the amplifier 42 and demodulator 44 required low-noise, high gain characteristics.

Referring now to FIG. 3, there is shown the detailed circuit components of the microbubble detector 60, including an operational amplifier 64 for receiving the output of the filter 44a and amplifying the amplified output being rectified by a diode D1 and filtered by a filter 65 comprised of resistors R4 and R5, and capacitor C3. The capacitor C1 and resistor R1 serve to isolate the input DC signal and in a similar fashion, the resistor R2 and capacitor C2 provide DC isolation for the other input of the operational amplifier 64. The output of the operational amplifier 64 is rectified by the halfwave rectifier D1 and any remaining high-frequency components are substantially removed by the filter 65 comprised of the resistors R4, R5 and capacitor $C_3$ to provide a DC signal input to a comparator 66. The operational amplifier 64 provides a sufficient amplification of the signal of the frequency-to-voltage converter 40 so that in the presence of air bubbles, the comparator 66 is actuated, but insufficient so that in the normal mode of operation in the absence of bubbles, the output of the converter 40, as amplified and rectified, will not actuate the comparator 66. In addition to providing a filtered DC signal to the comparator 66, the filter 65 prevents a signal resulting from the presence of relatively few microbubbles within the bloodflow from actuating the alarm 62. The time constant of the filter 65 is selected to be relatively long, illustrative in the order of one-half second. Thus, if there are only relatively few bubbles for a relatively short period of time, such a condition will not actuate the alarm 62. The filtered output in turn is applied to the comparator comprised of operational amplifier 66 which compares the filtered output with a reference signal applied to the other input of the operational amplifier 66.

In accordance with a significant aspect of this invention, it is recognized that the presence of microbubbles appearing in the blood directed through the conduit 24 increases the amplitude of the backscatter signal as derived from the receiving crystal 18 by a factor of approximately 30 over the amplitude of that signal for blood without gaseous bubbles therein. It has been found that to provide a comparator to detect at least a 10-fold and in one illustrative embodiment, a 15-fold increase, by approximately selecting the reference input to the comparator 66, a clear indication of microbubbles in the bloodflow can be discerned.

In turn, upon detection of the noted increase, the comparator 66 provides an output to the set input of an S-R flip-flop 68 which is set in response thereto to energize an alarm 62 comprised of a first alarm 62a which is energized to indicate the presence of microbubbles within the bloodflow. The alarm 62a will remain energized until the output of the comparator 66 falls below the measured threshold level and a reset impulse provided by switch 70 is applied to the reset terminal R of the flip-flop 68. By the inclusion of the flip-flop 68, the alarm 62a remains actuated until the attending physician returns and is notified that the bubbles are or have been present in the patient's blood, even if that condition has desisted. Upon return or becoming aware of the alarm, the physician will reset the switch 70; if the presence of the bubbles continues, the alarm 62 will again be energized. In any event, the physician is made aware that there were bubbles present and whether the condition is still present. During normal operation, the alarm 62b of the alarm 62 is energized. In one illustrative embodiment of this invention, the alarms 62a and 62b may provide both a visual and an audio indication.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. An ultrasonic wave system for measuring the characteristics of a liquid flowing through a conduit, said system comprising:

(a) first and second transducer elements operatively associated with the conduit for respectively transmitting an ultrasonic wave into the liquid flowing through the conduit and for receiving an ultrasonic wave backscattered by the liquid directed through the conduit;

(b) generator means for applying a high-frequency signal to said first transducer element causing it to emit the ultrasonic wave into the liquid;

(c) said second transducer element providing an electrical output signal of a frequency corresponding to that high frequency of said generator means, amplitude-modulated in accordance with the backscattered signal derived from the liquid, the frequency having been shifted from that high frequency of said generator means by the Doppler phenomenon, dependent upon the velocity of the liquid directed through the conduit and whose amplitude is dependent on the acoustic impedance of the liquid;

(d) first means coupled to receive the electrical output of said second transducer element for providing an amplitude demodulated output signal, bearing frequency components of the shifted frequency;

(e) second means responsive to an increase in the amplitude output of said demodulating means for providing an alarm manifestation indicating an increase in the acoustic impedance due to presence of gaseous bubbles within the liquid directed through the conduit; and (f) third means coupled to receive the output signal of said first means and responsive to the frequency shift for providing a manifestation of the rate of the liquid flow.

2. The ultrasonic wave system as claimed in claim 1, wherein the liquid directed through the conduit is blood and said second means is responsive to a 15-fold or greater increase for providing the alarm manifestation.

3. The ultrasonic wave system as claimed in claim 1, wherein said first transducer comprises an LTZ-1 crystal material and said second transducer comprises an LTZ-5 crystal material.

4. The ultrasonic wave system as claimed in claim 1, wherein said generator means applies an electrical signal having a frequency of approximately 3.13 MHz.

5. The ultrasonic wave system as claimed in claim 1, wherein said first means comprises a radio frequency amplifier for first amplifying the output of said second transducer element, and an amplitude demodulating circuit for providing an output in accordance with the amplitude modulation of the output signal derived from said second transducer element.

6. The ultrasonic wave system as claimed in claim 1, wherein said second means comprises a comparator for making a comparison between the amplitude of the output of said first means and a reference signal.

7. The ultrasonic wave system as claimed in claim 1, wherein there is further included means responsive to the frequency shift of the output of said demodulating means for providing a first alarm manifestation indicative of a liquid flow greater than a first, predetermined rate.

8. The ultrasonic wave system as claimed in claim 1, wherein said third means includes means responsive to the frequency shift in the output of said demodulating means for providing a second alarm manifestation indicative of a rate of liquid flow through the conduit below a second predetermined level.

9. The ultrasonic wave system as claimed in claim 1, wherein the liquid flowing through the conduit is a patient's blood, and wherein said third means comprises means responsive to the frequency shift in the output of said demodulating means for providing a first alarm manifestation indicative of a rate of blood flow through the conduit above a first level tending to rupture the patient's artery through which the blood flows, and a second alarm manifestation indicative of a rate of blood flow through the conduit below a second level that is insufficient for the patient.

10. An ultrasonic wave system for measuring the characteristics of a liquid flowing through a conduit, said system comprising:
  (a) first and second transducer elements operatively associated with the conduit for respectively transmitting an ultrasonic wave into the liquid flowing through the conduit and for receiving an ultrasonic wave backscattered by the liquid directed through the conduit;
  (b) generator means for applying a high-frequency signal to said first transducer element causing it to emit the ultrasonic wave into the liquid;
  (c) said second transducer element providing an electrical output signal of a frequency corresponding to that high frequency of said generator means, amplitude-modulated in accordance with the backscattered signal derived from the liquid, the frequency having been shifted from that high frequency of said generator means by the Doppler phenomenon, dependent upon the velocity of the liquid directed through the conduit and whose amplitude is dependent on the acoustic impedance of the liquid;
  (d) first means coupled to receive the electrical output of said second transducer element for amplitude demodulating its output; and
  (e) second means comprising a comparator for making comparison between the amplitude of the output of said first means and a reference signal for providing an alarm manifestation indicating an increase in the acoustic impedance due to presence of gaseous bubbles within the liquid directed through the conduit, and memory means coupled to the output of said comparator for providing a first output signal upon being actuated by the output of said comparator, a first alarm responsive to the first output signal to provide a visual manifestation of the presence of the gaseous bubbles within the liquid directed through the conduit, and a second alarm coupled to a second output of said memory means for providing an indication of the absence of gas bubbles within the liquid.

11. The ultrasonic wave system as claimed in claim 10, wherein said second means further comprises a first amplifier for amplifying the output of said first means, a rectifier for rectifying same and a filter, the filtered output being applied to the first input of said comparator.

12. The ultrasonic wave system as claimed in claim 11, wherein said filter is characterized by a time constant of sufficient duration to prevent the momentary presence of bubbles within the liquid from actuating said second means to provide the alarm manifestation.

* * * * *